(12) United States Patent
Guarnieri

(10) Patent No.: US 8,093,261 B2
(45) Date of Patent: Jan. 10, 2012

(54) RAPID RELEASE MINI-TABLETS PROVIDE ANALGESIA IN LABORATORY ANIMALS

(75) Inventor: Michael Guarnieri, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 779 days.

(21) Appl. No.: 11/876,102

(22) Filed: Oct. 22, 2007

(65) Prior Publication Data

US 2008/0096910 A1   Apr. 24, 2008

Related U.S. Application Data

(60) Provisional application No. 60/853,904, filed on Oct. 24, 2006.

(51) Int. Cl.
*A01N 43/42* (2006.01)
*A01N 43/40* (2006.01)
*A61K 31/44* (2006.01)
*A61K 31/445* (2006.01)

(52) U.S. Cl. ........................................ 514/289; 514/329

(58) Field of Classification Search .................. 514/289, 514/329
See application file for complete search history.

(56) References Cited

U.S. PATENT DOCUMENTS

| 4,164,560 A | 8/1979 | Folkman |
| 4,452,775 A | 6/1984 | Kent |
| 5,069,909 A * | 12/1991 | Sharma et al. ............... 424/449 |
| 5,137,874 A | 8/1992 | Cady |
| 5,188,827 A | 2/1993 | Black |
| 6,375,957 B1 | 4/2002 | Kaiko et al. |

FOREIGN PATENT DOCUMENTS

| EP | 1242087 | 9/2002 |
| WO | WO 96/15815 | 5/1996 |
| WO | WO 01/19403 | 3/2001 |
| WO | WO 03/013476 | 2/2003 |
| WO | WO 03/061632 | 7/2003 |

OTHER PUBLICATIONS

European Pharmacopoeia 5.0. Section 3.2.8. Sterile Single-Use plastic Syringes. Jan. 2005, pp. 314-315.*
Hudong. Houseold Auxiliaries Co., Ltd. Published online 2002, p. 1.*
Bohme, "Buprenorphine in a transdermal therapeutic system—a new option," *Clin Rheumatol*, 21: S13-S16(2002).
Christoph et al, "Broad analgesic profile of buprenorphine in rodent models of acute and chronic pain," *Eur. J. Pharmacol.* 507: 87-98(2005).
Cirimele, et al. "Evaluation of the One-Step ELISA kit for the detection of buprenorphine in urine, blood, and hair specimens," *Forensic Science International*, 143: 153-156(2004).
Clark, et al. "Evaluation of liposome-encapsulated oxymorphone hydrochloride in mice after splenectomy," Comp Med, 54: 558-563(2004).
Coria-Avila, et al."Cecum location in rats and the implications for intraperitoneal injections," Lab Animal 36: 25-30(2007).
Cowan, "Buprenorphine: new pharmacological aspects," *Int. J. Clin. Pract. Suppl.* Feb. 3-8, discussion 23-24(2003).
Cowan, et at. "The animal pharmacology of buprenorphine, an oripavine analgesic agent," *Br. J. Pharmacol.* 60: 547-554(1977).
Flecknell, "The relief of pain in laboratory animals," *Lab Animal*. 18: 147-160(1984).
Gades, et al., "The magnitude and duration of the analgesic effect of morphine, butorphanol, and buprenorphine in rats and mice," *Contemp Top Lab Anim Sci.* 39(2):8-13(2000).
Gopal, et al. "Characterization of the pharmacokinetics of buprenorphine and norbuprenorphine in rats after intravenous bolus administration of buprenorphine," *Eur. J. Pharmaceutical Sciences*, 15: 287-293(2002).
Grant, et al. "Prolonged analgesia and decreased toxicity with liposomal morphine in a mouse model," Anesthesia and Analgesia 79: 706-709,(1994).
Guarnieri et al, "Toxicity of intracranial and intraperitoneal O6-benzyl guanine in combination with BCNU delivered locally in a mouse model," *Cancer Chemotherapy Pharm.* 50: 392-396(2002).
Guarnieri, et al. "Flexible versus rigid catheters for chronic administration of exogenous agents into central nervous system tissues," *J Neuroscience Methods*, 144: 147-152(2005).
Hersh, et al. "Anesthetic activity of the lipospheres bupivacaine delivery system in the rat," Anesth Prog. 39(6)197-200(1992).
Karas, "Barriers to assessment and treatment of pain in laboratory animals," *Lab Anim* 35(7):38-45(2006).
Kogel et al, "Interaction of mu-opioid receptor agonists and antagonists with the analgesic effect of buprenorphine in mice," *Eur. J. Pain.* 9: 599-611(2005).
Krugner-Higby, et al. "Liposome-encapsulated oxymorphone hydrochloride provides prolonged relief of postsurgical visceral pain in rats," Comparative Medicine 53: 270-279(2003).
Liu, et al. "Novel depots of buprenorphine have a long-acting effect for the management of physical dependence to morphine," *J. Pharm. Pharmacol.* 58(3): 337-44(2006).

(Continued)

*Primary Examiner* — Paddy Padmanabhan
*Assistant Examiner* — Samira Jean-Louis
(74) *Attorney, Agent, or Firm* — Pabst Patent Group LLP

(57) ABSTRACT

Pellets containing an analgesic uniformly dispersed in a lipid carrier such as cholesterol mixed with fatty acid esters, can be used to provide long term pain relief. 5 mg cholesterol-tryglyceride-buprenorphine pellets released the majority of drug in 24-48 hours after implant and provide clinically significant plasma levels of analgesia in mice for 3-9 days. Blood levels of analgesia peak at day-1 and are substantially complete by day-5 depending on the level of buprenorphine. These results demonstrate that post surgical implants provide clinically significant levels of analgesia in the 24-48 hour period following surgery and thus obviate the time consuming, expensive, and high-risk need to inject mice post surgery. The pellets are safe and easy to use. Placed in the surgical wound at the end of surgery, they provide 2-3 days of analgesia and obviate the need for subsequent handling of the animal for pain therapy. The implants have no detectable effect on mouse behavior, hematology, or liver chemistry. The unexpected release kinetics of the 5 mg pellet provides an ideal implant for post surgical analgesia. These implants solve a significant problem facing scientists who use rodents in research and abide by international of animal welfare.

11 Claims, 1 Drawing Sheet

OTHER PUBLICATIONS

Liu, et al."Novel depots of buprenorphine prodrugs have a long-acting antinociceptive effect," *Anesth Analg.* 102: 1445-1451(2006).

Mohl, "The Development of a Sustained and Controlled Release Device for Pharmaceutical Proteins based on Lipid Implants." Dissertation, University of Munich, 2004.

Okumu et al."Sustained delivery of human growth hormone from a novel gel system: SABER," *Biomaterials* 23(22):4353-4358(2002).

Ozdogan et al, "The analgesic efficacy of partial opioid agonists is increased in mice with targeted inactivation of the alpha2A-adrenoceptor gene," *Eur. J. Pharmacol.* 529:105-113(2006).

Pontani and Misra, "A long-acting buprenorphine delivery system," *Pharmacol Biochem Behav.* 18:471-474(1983).

Pontani et al. "Disposition in the rat of buprenorphine administered parenterally and as a subcutaneous implant," *Xenobiotica*, 15, 287-297(1985).

Pontani, et al., "A long-acting buprenorphine delivery system," *Pharmacology Biochemistry & Behavior* 18:471-474(1983).

Richardson, et al. "Anaesthesia and post-operative analgesia following experimental surgery in laboratory rodents: are we making progress?" *Altern Lab Anim* 33:119-127(2005).

Shah, et al., "A biodegradable injectable implant for delivering micro and macromolecules using poly (lactic-co-glycolic) acid (PLGA) copolymers," *J. Control. Rel.* 27(2):139-147(1993).

Shaw et al, "Treatment of intractable cancer pain by electronically controlled parenteral infusion of analgesic drugs," Cancer. 1;72(11 Suppl):3416-25 (1993).

Silverman, "Did an audiotape squirrel away the minutes?," *Lab Animal*, 30(3):21-23(2001).

Toongsuwan, et al."Formulation and characterization of bupivacaine liposperes," *Int. J. Pharmaceutics* 280:57-65(2004).

* cited by examiner

RAPID RELEASE MINI-TABLETS PROVIDE ANALGESIA IN LABORATORY ANIMALS

CROSS-REFERENCE TO RELATED APPLICATIONS

This application claims priority to U.S. Ser. No. 60/853,904, filed Oct. 24, 2006.

FIELD OF THE INVENTION

This is generally in the field of controlled drug delivery, and in particular is a long term analgesic formulation for implantation in laboratory animals.

BACKGROUND OF THE INVENTION

Regulations for animal research require humane treatment of laboratory animals. Because animals cannot articulate pain, humane principles mandate that scientists provide the same analgesia that humans need for similar surgery. Indeed, an increasing body of evidence has shown that pain receptors in rodents and humans are virtually identical and that the sensation of pain would be highly comparable (Cowan, et al. Eur J Pharmacology, 507: 87-98, 2005). A second principal is that regulations for animal research be internationally harmonized so that pharmaceutical studies have the same scientific basis in every country.

The U.S. Department of Agriculture (USDA) regulates animal research in the US (Animal Welfare Act and Amendments, (7 U.S.C. 2131 et seq APHIS, USDA). With one exception, USDA regulations for animal welfare are similar to regulations in the Europe, Japan, and other industrialized nations. In the US, mice and rats are not considered to be "animals." This exception allows scientists in the US to provide lower and less expensive standards of analgesia. Studies have shown that at least 80% of scientists fail to provide adequate post-surgical analgesia for rodents (Richardson, et al. Altern Lab Anim 33: 119-127, 2005). Not surprisingly, the exception is the basis of anti-USDA lawsuits from animal welfare organizations.

It is estimated that more than 60 million mice and rats are used yearly in medical and toxicology research, with the majority of rodents being used in the US. The loophole in USDA regulations regarding the post surgical care of rodents may play a role in these use patterns. Many observers predict that US regulations will soon be come harmonized with international regulations and that rodents will be afforded greater protection based on scientific concerns and humane principles.

A low cost, safe and easy to use analgesic for rodent surgery could meet many of the concerns that have been articulated by scientists in the US. Scientists have defended their reluctance to use analgesia for rodents based on the expense of post-surgical care, concerns that analgesia could interfere with the outcome of an experiment, and the difficulty of handling small animals.

The cost of post-surgical care can be significant and the management of analgesia requires expensive labor resources. Drugs such as aspirin and ibuprofen must be given orally (PO) at 4-6 hour intervals. Morphine and buprenorphine have to be injected subcutaneously (SQ) or intraperitonealy (IP) at 6-8 hour intervals. Injured animals do not eat or drink on normal schedules, so food and water cannot be effectively spiked with drugs. Whether post-surgical analgesia affects the outcome of an experiment can be determined. Scientists routinely state their concerns that affects can occur (Karas Ariz., Lab Animal 35: 38-45, 2006). Frequently, these statements are made without experimental proof (Silverman J, Lab Animal, 30 (3): 21-26, 2001). It is highly doubtful that among the many choices of analgesic drugs, one or more drug could not be found to humanely treat the animal and not interfere with the experiment.

The difficulty in providing analgesia to small animals is perhaps the most significant barrier to rodent care. It is difficult to grab and hold a mouse and rat without disturbing the surgical wound, injuring the spine, and without causing more pain. Once restrained, animals resist PO therapy. SC and IP injections cause pain. IP injections cause infections and death if the needle penetrates sensitive tissue (Coria-Avila, et al. Lab Animal 36: 25-30, 2007.) A chronic delivery form of analgesia for rodent surgery would have significant benefits.

Several efforts have been made to use chronic drug-delivery systems such as infusion pumps and biodegradable scaffolds for laboratory and companion animal medicine. Alzet osmotic pumps and other swellable core technologies have become a standard method for delivering constant levels of drugs to animals for research (Guarnieri, et al. J Neuroscience Methods, 144: 147-152, 2005). Additional efforts have included the use of transderinal patches (Bohme Clin Rheumatol, 21: S13-S16, 2002), and food-based drugs. Transdermal patches have limited use because rodents and companion animals scratch and remove skin patches. Food-based analgesia has not been widely studied because post-surgical animals frequently have erratic eating patterns and because of the costs associated with adding drugs to standard chows.

An implantable, rapid-release analgesic would significantly reduce barriers to humane post surgical animal care. However, as demonstrated by the examples, most controlled release systems do not provide the necessary blood levels of analgesics required. Biodegradable drug implants would eliminate the safety concerns about handling small animals after surgery. Cholesterol implants have been used to provide sustained release of macromolecules, but not for the short-term delivery of analgesia (U.S. Pat. No. 4,452,775 to Kent. Liposheres for controlled delivery of substances have been described in U.S. Pat. No. 5,188,827 to Domb. Liposomes, solid lipid nanoparticles, oily suspensions, and fatty acids for sustained release parenteral formulations and implants have been described in U.S. Pat. No. 5,137,874 to Cady. Waxes, lipid microspheres, and lipid implants have been described as sustained-release vehicles, as reviewed by Mohl S, The Development of a Sustained and Controlled Release Device for Pharmaceutical Proteins based on Lipid Implants. Dissertation, University of Munich, 2004. In the majority of cases, the lipid and other biodegradable carrier such as PLGA copolymers (Shaw et al, 1993) are designed for the long-term sustained release of drugs and vaccines (U.S. Pat. No. 4,164,560 to Folkman and Langer.

Several exceptions can be noted to the focus of biodegradable lipid scaffolds and long-term drug delivery. Lidocaine and bupivcaine biodegradable scaffolds such as SABER and liposheres have been designed for 2-3 hour duration of anesthesia for surgical wounds (Hersh, et al. Anesth Prog. 39(6): 197-200, 1992; Toongsuwan, et al. Int J Pharmaceutics 280: 57-65, 2004). Liposomal preparations of morphine and oxymorphone have been tested in mouse and rat pain models (Grant, et al. Anesthesia and Analgesia 79: 706-709, 1994; Krugner-Higby, et al. Comparative Medicine 53: 270-279, 2003; Clark, et al. Comp Med, 54: 558-563, 2004). Liposomes, however are difficult to prepare and must be used fresh. Morphine is a more highly regulated drug and provides less analgesic efficacy compared to buprenorphine.

Buprenorphine esters can act as buprenorphine pro drugs in sesame, castor, cottonseed, peanut or soybean oil solutions injected into rat muscle (IM). The analgesic effect for sesame oil solutions could be measured for approximately 3 days (Liu, et al. Anesth Analg. 102: 1445-1451, 2006; J Pharm Pharmacol. 58(3): 337-34, 2006). The later studies contrast with our inability (Table 5) to detect buprenorphine in blood following SC injections of buprenorphine in oleic acid, an oil with properties highly similar to the oils used by Liu and coworkers.

Pontani, et al., Pharmacology Biochemistry & Behavior 18: 471-474, 1983 and Xenobiotica, 15, 287-297, 1985 describe a 50 mg cholesterol implant designed for the sustained release of buprenorphine for long-term therapy to prevent opiate seeking behavior. The 50 mg implant releases buprenorphine at a uniform rate (first order kinetics) for at least 12 weeks. While this release profile is suitable for sustained delivery of anti-addiction medication, it is highly unsuitable for short-term post surgical analgesia. The long-term presence of a foreign body and drug could have significant impact on research on vaccines, neurodegenerative disease, cancer, immunity-related chronic diseases such as diabetes, and other diseases.

It is therefore an object of the present invention to provide a controlled release formulation for delivery of analgesics to laboratory and research animals, especially small rodents.

SUMMARY OF THE INVENTION

Pellets containing an analgesic uniformly dispersed in a lipid carrier such as cholesterol mixed with fatty acid esters, can be used to provide long term pain relief. 5 mg cholesterol-tryglyceride-buprenorphine pellets released the majority of drug in 24-48 hours after implant and provide clinically significant plasma levels of analgesia in mice for 3-9 days. Blood levels of analgesia peak at day-1 and are substantially complete by day-5 depending on the level of buprenorphine. These results demonstrate that post surgical implants provide clinically significant levels of analgesia in the 24-48 hour period following surgery and thus obviate the time consuming, expensive, and high-risk need to inject mice post surgery. The pellets are safe and easy to use. Placed in the surgical wound at the end of surgery, they provide 2-3 days of analgesia and obviate the need for subsequent handling of the animal for pain therapy. The implants have no detectable effect on mouse behavior, hematology, or liver chemistry. The unexpected release kinetics of the 5 mg pellet provides an ideal implant for post surgical analgesia. These implants solve a significant problem facing scientists who use rodents in research and abide by international of animal welfare.

DETAILED DESCRIPTION OF THE INVENTION

Figure 1:
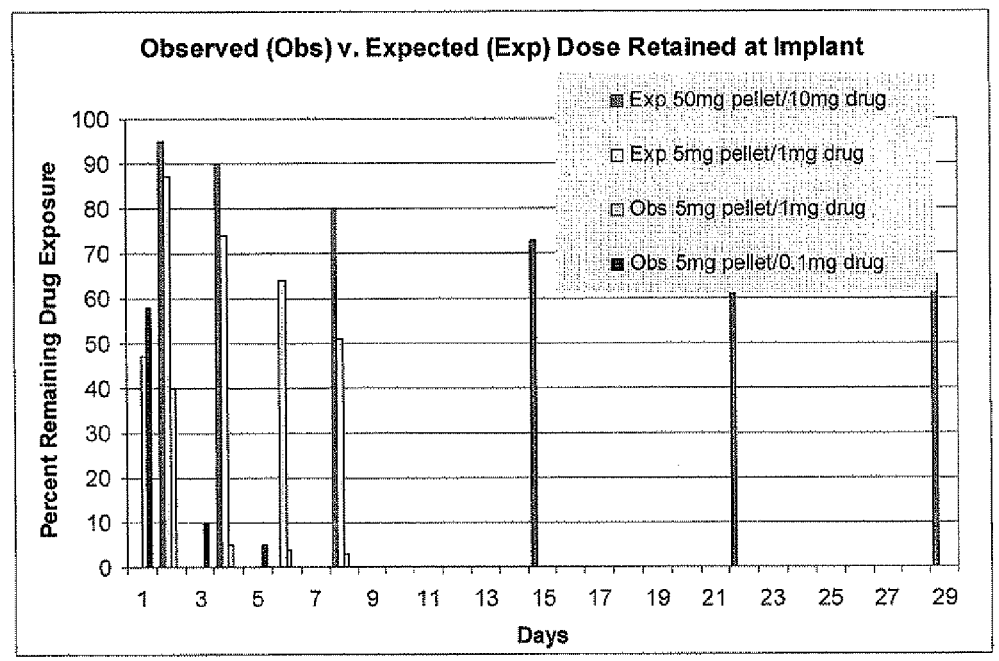
FIG. 1 is a graph of percent remaining drug over time in days comparing the pharmacokinetics of a prior art 50 mg pellet with a 5 mg pellet as described herein.

I. Formulations
  A. Analgesic
  Any of the opioids such as buprenorphine and butorphanol, or drugs such as fentanyl can be used. Representative local anesthestics include bupivacaine, ropivacaine, dibucaine, procaine, chloroprocaine, prilocalne, mepivacaine, etidocaine, tetracaine, lidocaine, and xylocalne, and mixtures thereof can also be used, alone or in combination with other analgesics.

In the preferred embodiment, buprenorphine is recommended for moderate to severe acute pain in mice and rats. The recommended dose in mice ranges from 0.05-2.0 mg/kg, SC q6-12 hrs (Flecknell, 2000), (Gades, Danneman et al., 2000). Recent studies have shown that the drug has a broad analgesic profile in a wide range of rodent models of acute and chronic pain [Christoph et al, Eur J Pharmacol 507: 87-98; 2005]. The mechanism of action has been studied in mice (Kogel, et al. Eur. J Pain, 9: 599-611, 2005; Ozdogan et al, Eur J. Pharmacol. 529:105-113; 2006). However, as with most studies of buprenorphine in rodents, these studies have aimed at understanding the drug's action in humans as a medication for treating heroine addiction.

The effective dosages for drugs other than buprenorphine can be calculated based on relative potencies of the various drugs. See, for example, EP 1242087 to Rechitt.

B. Pellet Composition

In the preferred embodiment, the formulation contains cholesterol or another natural or GRAS sterol. The cholesterol is mixed with a triglyceride or fatty acid ester such as glyceryl tristearate.

Other ingredients can be added, such as antibiotics and antiinflammatories. Representative antiinflammatories include glucocorticosteroids such as dexamethasone, cortisone, prednisone, hydrocortisone, beclomethasone dipropionate, betamethasone, flunisolide methylprednisone, paramethasone, prednisolone, triamcinolone, alclometasone, amcinonide, clobetasol, fludrocortisone, diflorasone diacetate, fluocinolone acetonide, fluocinonide, fluorometholone, flurandrenolide, halcinonide, medrysone and mometasone and pharmaceutically acceptable mixtures and salts thereof, and non-steroidal antiinflammatories such as rimadyl, and aspirin.

II. Method of Manufacture

The preferred method of manufacture is described below. Cholesterol and triglyceride are dissolved in a suitable solvent such as a halogenated solvent and alcohol (5:1), chloroform or methylene chloride, preferably chloroform, to form a liposome or liposphere, analgesic is added to the desired drug loading, the drug and carrier are mixed to form a uniform dispersion, and the solvent removed by evaporation or other techniques known to those in the art. The resulting dry powder is then compressed or extruded to form pellets, preferably less than 5 mm in diameter and length, more preferably 3 mm or less.

In the preferred embodiment, pellets are loaded with 0.1 to 50% by weight drug, more preferably 2-20% by weight drug. In a preferred embodiment, pellets contain approximately 5 mg:0.100 mg drug, to 5 mg-1.0 mg drug.

III. Method of Use

The pellets are implanted at the time of surgery, if possible, or immediately thereafter using a catheter or trocar. The pellets can be implanted IM, SC, or IP. The amount administered is based on an effective amount of anesthetic per kg animal weight, as demonstrated by the following examples. The preferred dosage for mice is between 0.5 and 2 mg/kg.

In the preferred embodiment, the animals are rodents such as mice, rats, gerbils, hamsters, rabbits or guinea pigs. Other animals can also be treated, such as dogs, cats, pigs, and livestock such as horses, goats, sheep, cattle and caeloids (lamas, alpaca, vicuna).

The product is sold as single use surgical implant or in a disposable loaded syringe.

The present invention will be further understood by reference to the following non-limiting examples. References cited herein are specifically incorporated by reference.

Materials and Methods

Animals: 6-8 week old female BalbC mice were purchased from Harlan, provided with Baltimore City water and standard pelleted chow, and maintained by the Johns Hopkins University Department of Comparative Medicine, Animal Care facility under a protocol approved by the Institute Animal Care and Use Committee.

Reagents: Chloroform (J. T. Baker (Hydrocarbon Stabilized) HPLC-grade was obtained from a Johns Hopkins University supply, ethanol was obtained from the Johns Hopkins Hospital supply. Solvents were used fresh. Cholesterol (Min. 99%, Sigma C 8667), glyceryl-tristearate (Approx. 99%, Sigma T 5061), oleic acid, and buprenorphine HCl (Sigma B 9275) were purchased from Sigma-Aldrich (St. Louis, Mo. 63178). Certificates of Analysis, Certificates of Origin, and Material Safety Data Sheets for each product are available at Sigma-Aldrich.com.

Pellet Preparation: Pellets were prepared using the technique previously described for preparing Gliadel wafers (Guarnieri, Cancer Chemotherapy and Pharmacology, 50, 392-396, 2002). The 20% (w:w) drug pellets were prepared by dissolving 360 mg of cholesterol, 40 mg of glyceryl tristearate, and 100 mg of buprenorphine in 50 mL chloroform and 15 ml of ethanol. 2% (w:w) drug pellets were prepared from 450 mg of cholesterol 40 mg of glyceryl stearate and 10 mg of buprenorphine in 50 mL chloroform and 15 ml of ethanol. Solvent solutions were evaporated using a Buchi roto-evaporator at reduced pressure and 37° water bath for 24 hours. No effort was made to monitor the evaporator vacuum or to monitor the water bath temperature.

In all cases, the resulting powders were dry, odorless, and easily transferred from the round bottomed evaporation flask with a sterile spatula. Using aseptic techniques, the resulting dry powders were transferred to a 15 mL screw-capped test tube and stored at −20° until used for pellet making. Pellets were pressed by allowing the drug powder to warm to room temperature and measuring 5±0.2 mg aliquots onto sterile weighing paper. The powder was transferred to a hand press having a 3 mm die. Pellets were pressed using approximately 2 tons of pressure for 15 seconds. The resulting 1×3 mm cylindrical pellets were stored at −20° before in vivo or in vitro tests.

Oleic Acid Emulsion: An oleic acid emulsion of drug was prepared by adding 500 mg of oleic acid from a freshly opened vial and 1 mg of drug to a 2 mL Eppendorf tube. A battery powered hand mixer with a polyethylene homogenizer was used for 30-60 seconds to blend the drug into the oil. The resulting emulsion was transferred immediately to a 1 mL syringe for injection into mice.

Dissolution Tests: Pellets in a screw capped test tube containing 10 mL of saline were placed in a 37° shaking water bath. At intervals described in Results, 1 mL aliquots of supernatant were removed and examined at 285 nm for buprenorphine.

Buprenorphine Measurements: Buprenorphine released into the saline solutions used for in vitro dissolution tests was measured at 285 nm in disposable cuvets using a standard curve prepared with 1 mg/ml solutions of buprenorphine in 1% ethanol in water. Buprenorphine in pellet and powders was measured by crushing the pellet using a glass spatula and mixing the powder in a 15 mL centrifuge tube with 1 mL of petroleum ether and 1 mL of 0.5 N HCl solution. The mixtures were vortexed for 15 seconds and centrifuged for 10 min at low speed to separate the solvent phases. The acidic aqueous phase was re-extracted 4 times for a total of 5 extractions to afford a clear aqueous phase which was examined at 285 nm for buprenorphine. The organic phases were discarded in laboratory chemical waste bottles for solvent recovery and recycling. Buprenorphine in plasma was measured by ELISA assay (Cirimele, et al. Forensic Science International, 143: 153-156, 2004). Kits were purchased from IDS (St. Joseph, Mich.).

Surgery: All procedures, including the mandibular bleed, are conducted under a standard protocol, MO05M56 (Section 3, Protocols), approved by the Johns Hopkins Animal Care and Use Committee. Surgery is performed with sterile equipment and aseptic conditions. Approximately 20 g mice are anesthetized with 0.15 mL of a solution containing ketamine and xylazine. A surgical surface on the right flank is shaved and washed with ethanol and Betadyne. A 4-5 mm incision is made through the skin. A drug pellet is inserted into the exposed SC cavity. The skin is apposed and stapled. Animals are observed until conscious and moving normally as specified in the standard protocol. They are returned to their cages. At intervals described in Results, approximately 100 μL of blood is collected by mandibular bleeds for drug analyses and/or toxicity tests.

Clinical Chemistry: Samples of blood were analyzed for hematology and liver chemistry. Blood samples were collected 4-5 days before surgery to provide baseline control values. Tests were performed by the Mouse Phenotyping Core of the Johns Hopkins University School of Medicine Department of Molecular and Comparative Pathobiology. A liver panel measures total protein, albumin, glucose, and the enzymes alkaline phosphatase, alanine aminotransferase, and aspartate aminotransferase. The hematology panel included platelets, hemoglobin, red and white cell indices, and white cell differential.

Pain Assessments Pain was measured using the revised ethnogram described by Krugner-Higby et al (2003) for measuring post surgical pain in rats (Krugner-Higby, et al. Comparative Medicine 53: 270-279, 2003). Animals were observed daily for behavior, hair coat, eye appearance, and porphyrin staining.

Weight: Mice were weighed before and after implant using a Mettler portable laboratory balance with a 0.01 gram read out.

Results

In vitro dissolution studies of the 5 mg pellets containing 1.0 mg concentration of buprenorphine are shown in Table 1. Results are expressed as the average of 3-4 samples for each sustained-release product. For comparison, the dissolution of 5 mg pellets of SABER (Okumu et al. Biomaterials 23 (22): 4353-4358, 2002.) and PCPP:SA (lactic-co-glycolic) acid copolymer (Shah et al., J Control Rel. 27(2): 139-147, 1993) were also examined, each containing 1 mg of buprenorphine in the 5 mg pellet.

The in vitro data shown in Table 1 confirm the in vivo studies that cholesterol pellets release buprenorphine at a constant rate. For comparison release studies with SABER and PCPP:SA biodegradable scaffolds show similar dissolution rates. The three sustained-release scaffolds provided buprenorphine at approximately first-order release kinetics. At least 50% of the dose remains in the animal 7-days after implant.

TABLE 1

Cumulative Buprenorphine Release at 37° in PBS from 5 mg Cholesterol Pellet, PCPP:SA, and SABER Pellets

| Scaffold | Day 1 | Day 3 | Day 5 | Day 7 |
|---|---|---|---|---|
| | | % Drug Released | | |
| Cholesterol Pellet (20% w:w) | 13 | 26 | 36 | 49 |
| PCPPSA | 10 | 22 | 34 | 50 |
| SABER-15% EtOH | 12 | 29 | 40 | 49 |

In vivo studies were conducted with 5 mg cholesterol pellets containing 1.0 mg of buprenorphine to investigate the safety in mice of a near lethal dose of buprenorphine (50 mg/kg). In the first set of tests, 9 mice were implanted with 5 mg pellets. Mice were observed daily for the first week and at 2-3 day intervals thereafter, and were bled on days-1, 2, 4, 7, 14, and 22.

One mouse died during bleeding on day-4. A second mouse died during bleeding on day-7. Autopsy reports suggest the cause of death was blood loss and spinal cord trauma due to excess pressure on the back of the mouse as the technician attempted to grab the mouse for bleeding. There was no evidence of pathology associated with the implants. The remaining animals were unremarkable. The animals were sitting in normal position, moving freely, grooming, bright and alert. Hair coat was normal. The eyes were open and alert. There was no evidence of porphyrin staining around the eyes or nose. There was no change in weights compared to two control mice that had surgery but no implants. The animals were euthanized 2 months after implant.

In a second safety study, eight mice were dosed with 5 mg pellets containing 1 mg of drug prepared as described above. Two animals were controls. Animals were observed daily for the first week and at 2-3 day intervals thereafter. There was no remarkable change in behavior. Animal weights at day-0 and day-5 were the same. Because the two deaths in Test 1 were suspected to be related to excessive bleeding (autopsy report), we limited blood collections to Ca 100 µL/48 hrs. The zero-time samples reported below represent samples of blood drawn 2-4 days before surgery.

Five mice (4 test, 1 control) were bled on days-0, 1, 3, 5, 7, and 14 for hematology. Five mice (4 test, 1 control) were bled on days-0, 1, 3, 5, 7, 14, 31, and 38 for liver function tests. Hematology tests were conducted to establish baseline values and to rule out effects of the procedure on sensitive bone marrow metabolism. Liver function tests were selected because the drug is metabolized in the liver.

Hematology parameters were largely normal. By day-5, mice began to exhibit increased white and red blood cell counts, a well-known effect in sequentially bled mice. Liver function parameters were largely normal. Alkaline phosphatase values were consistently, but slightly, out of range in test and control animals including the day-0 samples. To rule out hepatotoxicity, the liver function tests were extended to day-38. There was no significant difference between day-0 and day-38 values.

In summary, the results of the behavioral studies, weight, and blood tests showed no difference between animals dosed with a 1 mg of buprenorphine and control animals.

To investigate whether in vivo release kinetics would be similar to the in vitro data shown in Table 1, blood samples were analyzed for buprenorphine using an ELISA assay. The results in Table 2 show entirely unexpected results. In contrast to the in vitro dissolution tests in Table 1 and to results reported in rats with 50 mg cholesterol pellets containing 10 mg of drug there is a hyperbolic release of drug on day-1 to day-2 followed by a linear decline to day-14. By day-22 blood levels fall below the level of detection.

TABLE 2

Plasma Buprenorphine with Chronic Delivery of 1 mg Buprenorphine in Cholesterol/Triglyceride Pellet
Plasma Buprenorphine (ng/mL ± SD)
Post-Delivery Day

| 1 | 2 | 4 | 7 | 14 | 22 |
|---|---|---|---|---|---|
| 140 ± 29 | 120 ± 28 | 16 ± 8 | 11 ± 7 | 9 ± 5 | 0.2 ± 0.2 |

* n = 4 for day-0; 9 for days 1-4; 7 for days 7 to 22 for day

The results shown in Table 2 were confirmed in a second set of blood assays using samples of blood remaining after the hematology and liver function tests in the second safety study were measured for drug. Sufficient blood was not available from day-1 samples and for only about half of the remaining samples. Nonetheless, the results shown in Table 3 demonstrate that the in vivo release profile was similar to the bioavailability seen in Table 2.

TABLE 3

Repeat Plasma Buprenorphine with Chronic Delivery of 1 mg Buprenorphine in Cholesterol/Triglyceride Pellet
Plasma Buprenorphine (ng/mL ± SD)*
Post Delivery Day

| 1 | 3 | 5 | 7 | 31 |
|---|---|---|---|---|
| ** | 24 ± 24 | 13 ± 14 | 7.2 ± 1.6 | 0.0 | n = 2 for day-0, 2 for day-3, 5 for days 5 and 7;
** no sample available for test To determine whether the hyperbolic release kinetics seen in the in vivo studies using pellets with 1 mg of drug would be observed in studies with a cholesterol pellet containing a therapeutic level of buprenorphine, eight mice were dosed with a 5 mg pellet containing 0.1 mg of drug. Two animals were controls. The results, shown in Table 4 demonstrate that the proposed BPP affords clinically relevant plasma levels of buprenorphine for up to 72 hours.

TABLE 4

Plasma Buprenorphine with Chronic Delivery of 0.1 mg Buprenorphine in Cholesterol/Triglyceride Pellets
Plasma Buprenorphine (ng/mL ± SD)*
Post-Delivery Day

| 1 | 3 | 5 | 9 |
|---|---|---|---|
| 16 ± 16 | 10 ± 14 | 1.5 ± 2.5 | 0 |

TABLE 5

Plasma Buprenorphine with Chronic Delivery of 0.1 mg Buprenorphine in Cholesterol/Triglyceride Pellets Prepared without Solvents and in Oleic Acid Emulsions
Plasma Buprenorphine (ng/mL ± SD, n = 8)
Post-Delivery Day

| | 1 | 2 | 4 |
|---|---|---|---|
| No Solvents | 6 ± 2 | 0.5 ± 2 | 0 |
| Oleic Acid | 2 ± 1 | 0 | 0 |

Cholesterol pellets were prepared without solvents by mixing 90 mg cholesterol, 8 mg triglyceride, and 2 mg buprenorphine for 48 hours at 5° on a roller wheel. Eight 1-2 mg samples were collected randomly and assayed for buprenorphine to verify the homogeneity of the mixture. Five mg pellets were pressed and implanted in 8 mice. The blood levels of buprenorphine at days 1-4 are shown in Table 5. Cholesterol pellets prepared without chloroform-ethanol solution had significantly less capacity to provide sustained release analgesia. By day-2, blood levels of drug on average were less than 0.5 ng/per mL. Oleic acid emulsions of drug injected SC afforded a similar failure to provide sustained-release analgesia. The data in Table 5 shows that blood levels of drug from the 50 uL injections were 3-fold less compared to the solvent-free cholesterol pellet implant. There was no detectable buprenorphine at day-2.

Discussion

Buprenorphine arguably is the least likely analgesic drug to interfere with animal research. The work of Martin and colleagues in 1976 on chronic spinal injury in dogs confirmed the drug's action as a partial agonist at the mu-opioid receptor. Interest in the drug for more than 30 years relates to its unique pharmacology, including low toxicity, high affinity to and slow release from mu-opioid receptors, and dose-response curve in rodents [Flecknell, Lab Animal. 18: 147-160; 1984; Cowan, Int J Clin Pract Suppl. February: 3-8, discussion 23-24; 2003].

Buprenorphine esters can act as buprenorphine pro drugs in sesame, castor, cottonseed, peanut or soybean oil solutions injected into rat muscle (IM). The analgesic effect for sesame oil solutions could be measured for approximately 3 days (Liu, et al. Anesth Analg. 102: 1445-1451, 2006; J Pharm Pharmacol. 58(3): 337-34, 2006). The later studies contrast with the inability described herein (Table 5) to detect buprenorphine in blood following SC injections of buprenorphine in oleic acid, an oil with properties highly similar to the oils used by Liu and coworkers.

The studies described herein demonstrate that short term release of buprenorphine from cholesterol-triglyceride implants is safe. Safety is clearly demonstrated via clinical chemistry studies of liver enzymes. In all species tested, the drug is metabolized in the liver. The primary metabolite is norbuprenorphine. Pharmacokinetic studies have been conducted in rats. After bolus intravenous administration, plasma levels decline triexponentially. Unmetabolized drug excreted in the urine and feces one week after injection was 1.9 and 22.4% of the dose, respectively, and 92% of the dose was accounted for in one week (Pontani Xenobiotica, 15, 287-297, 1985). The plasma half-lives for buprenorphine and norbuprenorphine are about 4-5 hours (Gopal, et al. Eur J Pharmaceutical Sciences, 15: 287-293, 2002). The $LD_{50}$ for a bolus IP dose of buprenorphine in mice and rats is ca 95 and 200 mg/kg, respectively (Cowan, et al. Br J Pharmacol, 60: 547-554, 1977). In the present study, near-lethal doses of drug given via cholesterol-triglyceride implant, produced no signs of toxicity. Doses of 1 mg of drug, 50 mg/kg, had no effect on behavior or on sensitive liver enzymes that are involved in drug metabolism.

The unexpected and surprising difference in drug availability from 50 mg and 5 mg cholesterol-triglyceride implants is illustrated in FIG. 1. FIG. 1 shows the amount of drug retained at the implant site from 50 mg versus 5 mg pellet implants. The data for the 50 mg implant is taken from the report of Pontani and Misra (1983) using their in vivo data and their formula for the first-order release kinetics of 10 mg of buprenorphine from their 50 mg pellet: "Exp 50 mg pellet/10 mg drug." The plot of the in vitro data with 5 mg pellets containing 1 mg of drug (Table 1) is shown in FIG. 1 for comparison. The in vitro data with 5 mg pellets, "Exp 5 mg pellet/1 mg drug," closely matches the Pontani and Misra data.

Therefore, it was expected that while 5 mg pellets may afford some long-term possibilities for analgesia, the animals still would require 1 to 2 days of post-surgical injections at 6-8 hour intervals. Moreover, these 50 mg and/or 5 mg analgesic pellets could not be used in many research projects because the remaining somatic drug-load could interfere with metabolic and nerve studies. For example: the in vitro data argues that a 5 mg pellet with 1 mg of buprenorphine would hold 50% of the dose at day-7, or 25% of the lethal dose for mice.

As shown in FIG. 1, the observed in vivo data was strikingly different than expected. The 5 mg implants with 1.0 and 0.1 mg of drug (data from Table 2 and 4, respectively) had their maximum drug release in day-1 to day-2. Following this burst analgesia, the animals get the maximum pain therapy in the 24 hours after surgery. Moreover, there is little detectable drug remaining at day-5 to day-7. Thus, there is little concern that the analgesia can interfere with research objectives in laboratory experiments.

The unexpected and surprising difference in drug availability from 50 mg and 5 mg cholesterol-tryglyceride implants remains unexplained. While it is likely that the 3 mm by 1 mm long 5 mg pellet would erode faster than the 3 mm by 6 mm long 50 mg pellet described by Pontani and Misra (1983), one would expect similar release kinetics because in vitro tests with 5 mg pellets showed a release profile (Table 1) comparable to the 50 mg pellet in vivo. It is not believed that the hardness of the pellet played a role. Optimal pressure was used to prepare the pellets because more force and longer compaction prevented uniform pellet formation, possibly due to thermal effects on the lipid matrix. Also, given the same composition and production pressure, a smaller pellet should be harder and dissolve more slowly. If size and shape were the determining factor, one would expect to see the most rapid release with buprenorphine in oleic acid oil. Yet, little or no drug was detected in plasma one day after an implant with oleic acid, although based on the 5 hr half-life of the drug in plasma, at least 12.5 µg of buprenorphine should be available. The remarkably different blood levels of drug observed from cholesterol-tryglyceride-drug implants prepared by the solvent-evaporation method and implants prepared by blending ingredients without solvent (Table 5) suggest that buprenorphine and/or the triglyceride in organic solvent affords a unique particle.

One concern about the 50 mg implant is that it takes 12 or more weeks to dissolve in vivo. A second concern is that in vivo tests demonstrate first order kinetics for drug release. The slow linear release of drug means that the animal still would need several bolus injections of buprenorphine within the 24-hour period after surgery when pain is greatest.

In vitro dissolution tests demonstrated a linear drug release profile for the 5 mg pellet. It is logical to anticipate that it would have the same in vivo release deficiencies for analgesia as the 50 mg implant. However, in vivo mouse studies demonstrated entirely different and unexpected results. The 5 mg implants containing 0.1 mg of drug mice dissolved in approximately 3 days. Moreover, the in vivo studies demonstrated highly desirable burst kinetics. Plasma levels of drug peaked at day-1, a drug level that obviates the need for bolus injections of analgesia immediately after surgery.

While the surprising difference between the in vivo and in vitro results remains unexplained, the data unequivocally demonstrate that 5 mg implants can be used safely, and the 5 mg implants provide effective short-term analgesia for mouse surgery. Moreover, the product solves the challenge of providing post-surgical analgesia to small animals, a problem that has been known for more than 25 years. The 5 mg implant for the first time provides medical scientists with an easy-to-use, safe tool to meet international animal welfare regulations and national guidelines.

I claim:

1. A formulation for administration of an effective amount of analgesic anesthetic to an animal to provide pain relief over a period of between two days and nine days, consisting essentially of
   a lipophilic carrier consisting of a sterol and fatty acid ester, and
   an analgesic selected from the group consisting of local anesthetics, opioids, fentanyl, and butorphanol,
   wherein the analgesic is uniformly distributed in the carrier in a loading of 0.1 to 50% by weight, and
   the formulation is in the form of a dry powder, dispersion or pellets or tablets compressed from dry powder or extruded and less than five mm in length or diameter,
   wherein the formulation releases analgesic to provide clinically significant levels of analgesia for a period of between two and nine days and wherein release of analgesic is at least 92% complete over a period of between two and nine days.

2. The formulation of claim 1 wherein the analgesic is an opioid.

3. The formulation of claim 2 wherein the analgesic is buprenorphine.

4. The formulation of claim 1 wherein the carrier is a mixture of cholesterol and fatty acid ester.

5. The formulation of claim 1 wherein the analgesic is added to between 0.1 and 50% by weight.

6. The formulation of claim 1 in a single use syringe.

7. A method of making a formulation for administration of an effective amount of analgesic anesthetic to an animal to provide pain relief over a period of between two days and nine days, comprising
   Providing a solution of a lipophilic carrier consisting of a sterol and fatty acid ester,
   mixing uniformly into the carrier an analgesic selected from the group consisting of local anesthetics, opioids, fentanyl, and butorphanol in a loading of 0.1 to 50% by weight,
   removing the solvent from the mixture, to yield a formulation consisting essentially of a carrier consisting of a sterol and fatty acid ester and analgesic uniformly distributed therein, and
   forming the formulation into a dry powder, dispersion or pellets or tablets compressed from dry powder or extruded and less than five mm in length or diameter,
   wherein the formulation releases analgesic to provide clinically significant levels of analgesia over a period of between two and nine days, and wherein release of analgesic is at least 92% complete over a period of between two and nine days.

8. A method of providing pain relief in an animal comprising administering to the animal an effective amount of a formulation to provide pain relief over a period of between two days and nine days, the formulation consisting essentially of
   a lipophilic carrier consisting of a sterol and fatty acid ester, and
   an analgesic selected from the group consisting of local anesthetics, opioids, fentanyl, and butorphanol,
   wherein the analgesic is uniformly distributed in the carrier in a loading of 0.1 to 50% by weight, and the formulation is in the form of a dry powder, dispersion or pellets or tablets compressed from dry powder or extruded and less than five mm in length or diameter,
   wherein the formulation releases analgesic to provide clinically significant levels of analgesia over a period of between two and nine days and wherein release of analgesic is at least 92% complete over a period of between two and nine days.

9. The method of claim 8 wherein the formulation is administered at the time of surgery or by implantation or injection through a catheter or trocar.

10. The method of claim 9 wherein the formulation is administered intramuscularly, subcutaneously, or intraperitoneally.

11. The formulation of claim 1, wherein the formulation is in the form of a dry powder.

* * * * *